United States Patent
Gabele (10) Patent No.: US 8,172,887 B2
(45) Date of Patent: May 8, 2012

(54) LOCK AND RELEASE MECHANISM FOR A STERNAL CLAMP

(76) Inventor: Lorenz Gabele, Sauldorf (DE)

( * ) Notice: Subject to any disclaimer, the term of this patent is extended or adjusted under 35 U.S.C. 154(b) by 246 days.

(21) Appl. No.: 12/454,768

(22) Filed: May 22, 2009

(65) Prior Publication Data

US 2009/0240251 A1 Sep. 24, 2009

Related U.S. Application Data

(63) Continuation of application No. 11/339,369, filed on Jan. 25, 2006, now abandoned.

(60) Provisional application No. 60/646,732, filed on Jan. 25, 2005.

(51) Int. Cl.
*A61B 17/84* (2006.01)

(52) U.S. Cl. ......... 606/324; 606/105; 606/326; 606/328

(58) Field of Classification Search ............... 606/60, 606/280, 70, 71, 300, 74, 324, 326, 328, 606/105; 403/2, 43–46, 104, 105–108, 109.1–109.5
See application file for complete search history.

(56) References Cited

U.S. PATENT DOCUMENTS

| | | |
|---|---|---|
| 408,080 A | 7/1889 | Carroll |
| 2,688,351 A | 9/1954 | Sweet |
| 3,385,299 A | 5/1968 | Roy |
| 3,971,384 A | 7/1976 | Hasson |
| 4,201,215 A | 5/1980 | Crossett et al. |
| 4,512,346 A | 4/1985 | Lemole |
| 4,583,541 A | 4/1986 | Barry |
| 4,730,615 A | 3/1988 | Sutherland et al. |
| 4,794,675 A | 1/1989 | Bisconti |
| 4,863,476 A | 9/1989 | Shepperd |
| 4,896,668 A | 1/1990 | Popoff et al. |
| D309,350 S | 7/1990 | Sutehrland et al. |
| 5,139,498 A | 8/1992 | Astudillo Ley |
| 5,163,598 A | 11/1992 | Peters et al. |
| 5,263,973 A | 11/1993 | Cook |
| 5,352,225 A | 10/1994 | Yuan et al. |
| 5,437,685 A | 8/1995 | Blasnik |
| 5,439,463 A | 8/1995 | Lin |
| 5,462,542 A | 10/1995 | Alesi, Jr. |
| 5,672,177 A | 9/1997 | Seldin |
| 5,766,218 A | 6/1998 | Arnott |
| 5,810,854 A | 9/1998 | Beach |
| 5,928,231 A | 7/1999 | Klein et al. |
| 5,941,881 A | 8/1999 | Barnes |
| 5,964,762 A | 10/1999 | Biedermann et al. |
| 6,117,135 A | 9/2000 | Schlapfer |
| 6,217,580 B1 | 4/2001 | Levin |
| 6,969,398 B2 | 11/2005 | Stevens et al. |
| 7,033,377 B2 | 4/2006 | Miller, III |
| 2003/0083694 A1* | 5/2003 | Miller, III ............... 606/216 |
| 2004/0133206 A1 | 7/2004 | Stevens et al. |
| 2005/0267475 A1 | 12/2005 | Miller, III |
| 2005/0277939 A1 | 12/2005 | Miller, III |

* cited by examiner

*Primary Examiner* — Thomas J Sweet
*Assistant Examiner* — Ellen C Hammond
(74) *Attorney, Agent, or Firm* — Thomas C. Saitta (57) ABSTRACT

An engagement mechanism for a sternal clamp, the mechanism allowing for an open status where the clamp may be lengthened or shortened, a closing status where the clamp may only be shortened, and a locked status where the clamp cannot be lengthened or shortened, and wherein the device can be disposed in the locked status in differing overall lengths.

12 Claims, 6 Drawing Sheets

LOCK AND RELEASE MECHANISM FOR A STERNAL CLAMP

This application is a continuation of U.S. Non-Provisional patent application Ser. No. 11/339,369, filed Jan. 25, 2006, now abandoned, further claiming the benefit of U.S. Provisional Patent Application Ser. No. 60/646,732, filed Jan. 25, 2005.

BACKGROUND OF THE INVENTION

The invention relates generally to the field of lock and release mechanisms for telescoping or sliding paired members, more particularly relates to such mechanisms that allow the paired members to have three operational settings—a locked status precluding relative movement of the member pair, a closing status allowing relative movement of the paired members only in the direction toward each other to shorten the overall length of the combination of members, and a free travel status whereby the paired members can be moved in either direction relative to each. More particularly, the invention relates to such devices that utilize engaging opposing teeth of a ratchet bar type of construction. In particular, the invention is applicable for use with a sternal clamp device, and such an application shall be utilized to describe the invention herein.

A sternal clamp is a device that is used to secure two lateral halves of a sternum that has been longitudinally severed and divided in surgery, such as is often required to provide access to the interior of the chest cavity. The sternal clamp comprises a pair of sliding or telescoping clamp members, with each paired clamp member having means to grasp or abut the exterior edge of the sternum, such as a single or multiple leg or hook members extending to the rear of the clamp member. The sternal clamp device is positioned across the sternum with the hook members positioned between adjacent ribs. The two clamp members are then compressed, i.e., moved toward each other in sliding fashion, to shorten the device and thereby pull the sternal halves together. The clamp members are then locked or secured in this contracted position by various mechanical means. Examples of sternal clamps can be seen in U.S. Pat. No. 4,201,215 to Crossett et al., U.S. Pat. No. 4,279,248 to Gabbay, U.S. Pat. No. 4,802,477 to Gabbay, U.S. Pat. No. 5,928,231 to Klein et al., U.S. Pat. No. 6,007,538 to Levin, U.S. Pat. No. 6,051,007 to Hogendijk et al., U.S. Pat. No. 6,217,580 to Levin, and U.S. Pat. No. 6,540,769 to Miller, III.

A problem with the known devices is that the locking mechanisms utilized to maintain the sternal clamp in the compressed or contracted position are typically cumbersome, difficult to adjust and difficult to remove. Some mechanisms are not releasable at all once the clamp has been compressed. Some mechanisms do not allow the clamp members to be extended once the device has been compressed. Some mechanisms require the use of screws or similar fasteners that can be dropped or lost by the surgeon during the clamping step. All of these problems are exacerbated in emergency situations where immediate removal of the sternal clamp is required, such that in many cases destruction of the clamp by sawing or the like is the only suitable method for rapid access.

It is an object of this invention to provide a lock and release mechanism that enables the sternal clamp to have three functional statuses or settings—a first status where the device is locked to preclude relative movement of the clamp members in either direction, a second status where the device can be compressed or shortened by sliding the clamp members toward each other, but where release or extension of the device is precluded, and a third status where movement of the clamp members in either direction is allowed, to the point where the clamp may even be disassembled. It is a further object to provide such a device where the status of the sternal clamp may be easily and quickly changed from one status to either of the remaining statuses, and where any status may be chosen at any time. It is a further object to provide such a device where removal of the device from the patient can be quickly and easily accomplished at any time.

SUMMARY OF THE INVENTION

The invention is a locking and release mechanism and sternal clamp comprising this lock and release mechanism, where the sternal clamp comprises a pair of opposing clamp members, the clamp members cooperating with each other in a sliding or telescoping manner such that the sternal clamp can be shortened, contracted or compressed by relative sliding movement of the clamp members toward each other, and where the sternal clamp can be extended or disassembled by relative sliding movement of the clamp members away from each other. In this manner the sternal clamp may have a locked, closing or open status. One or more hook or leg members are connected to each of the clamp members such that opposite sides of a sternum can be abutted with the hook members in order to secure the longitudinally divided sternal halves in abutting relationship.

The lock and release mechanism comprises an engagement means and a status control means. The engagement means comprises a spring biased engagement arm pivotally mounted to one of the clamp members. The engagement arm is provided with engagement teeth that cooperate with engagement teeth of a ratchet bar disposed on the other of the clamp members. The status control means controls the position and freedom of movement of the engagement arm, such that the status control means can be adjusted to determine whether the device is in the locked, closing or open status. The status control means comprises a rotating member having a cam follower disposed within a cam opening provided in the engagement arm. The cam opening is of a non-symmetrical shape, such that with the cam following oriented in a first position, designated as the open status, the engagement arm is pivoted and held free of the clamp engagement teeth such that relative movement of the two clamp members is not precluded or controlled in either direction. With the cam follower oriented in a second position, designated as the closing status, the teeth of the engagement arm mate with the clamp engagement teeth, but the engagement arm is allowed limited travel away from the clamp engagement teeth such that the clamp members can be slid together. With the cam follower oriented in a third position, designated as the locked status, the teeth of the engagement arm mate with the clamp engagement teeth, but the engagement arm is prevented from traveling away from the clamp engagement teeth, thereby preventing relative movement of the clamp members in either direction. The status of the device can be changed from one to the other at any time.

DETAILED DESCRIPTION OF THE INVENTION

With reference to the drawings, the invention will now be described in detail with regard to the best mode and the preferred embodiment. In general, the invention is a locking and release mechanism and a sternal clamp comprising this mechanism, the sternal clamp comprising a pair of opposing clamp members that engage in a sliding or telescoping manner, whereby the sternal clamp can be placed into an open, closing or locked status. In the open status, the sternal clamp can be lengthened or shortened by bringing together or pulling apart the paired clamp members, as well as disassembled by fully separating the clamp members from each other. In the closing status, the clamp members can only be pushed together such that the sternal clamp can be shortened, but the clamp members cannot be pulled apart to lengthen the sternal clamp. In the locked status, the clamp can be neither lengthened nor shortened as relative movement of the clamp members is precluded.

The sternal clamp 100 comprises a first clamp member 10 and a second clamp member 20 that mate or engage in a sliding or telescoping manner such that the length or overall longitudinal dimension of the sternal clamp 100 can be adjusted as required, and preferably such that the clamp members 10 and 20 are fully separable from each other. The first or superior clamp member 10 comprises a main body 11, generally flat and thin. Sternum engaging means, such as one or more leg or hook members 12, are connected to the exposed free or outer end of the clamp body 11 and extend in a generally perpendicular manner to the rear of the main body 11. The second or inferior clamp member 20 likewise comprises a main body 21, generally flat and thin, with sternum engaging means, such as one or more rearward extending leg or hook members 22, connected to the free outer end of the clamp body 21. Pivot means, such as a relatively short pivot post 25, is mounted on the main body 21 of the second clamp member 20 to receive the engagement means 40. The two main bodies 11 and 21 are constructed to have sufficient separation, such as through the presence of a gap or slot, such that the pivot post 25 and the engagement means 40 reside between the two main bodies 11 and 21 when the sternal clamp 100 is greatly contracted. An aperture is provided in main body 21 to receive the post 51 of the status control means 50.

Sliding or telescoping means 30 are provided such that relative linear movement between the clamp members 10 and 20 is permitted in the longitudinal direction. As shown, the sliding means 30 may comprise a tongue member 31 disposed on each of the opposing edges of the first clamp member main body 11, the tongue members 31 mating with groove members 32 formed by shoulder members 33 disposed on each of the opposing edges of the second clamp member main body 21. Equivalent structures for the sliding means 30 are possible.

One part of the lock and release mechanism comprises engagement means 40, which comprises a biased pivoting engagement arm 41 provided with a pivot aperture 43 corresponding in size to the pivot post 25 of the second clamp member 20, such that the engagement arm 41 is retained on and may pivot in a plane parallel to the upper surface of the second clamp main body 21. One or more engagement teeth 42, preferably a plural number in linear alignment, are disposed on the outer edge of the engagement arm 41. A cam opening 46 of non-symmetrical shape is positioned in the base of the engagement arm 41 on the opposite side of the pivot aperture 43 from the engagement teeth 42. Extending from the engagement arm 41 and generally adjacent the cam opening 46 is curved spring segment 45, a thin biasing member that joins the engagement arm 41 to the spring body 44. Spring body 44 comprises a member that is restrained in a controlled position relative to the second clamp main body 21 by suitable means, such as by abutment with a stop member 23 disposed on the upper surface of second clamp main body 12. The combination of the spring body and the spring segment 45 creates a biasing force against the engagement arm 41 such that the engagement arm 41 is pushed outwardly toward the ratchet bar 13 of the first clamp member 10.

The other part of the lock and release mechanism comprises status control means 50, which comprises a means to select or initiate one of the three status positions available. As shown, status control means 50 comprises a post member 51 that is inserted through an aperture in the second clamp main body 21. A head 53 is joined to the post 51 and a slot 54 is disposed on the head 53 such that the head 53 and post 51 can be rotated by use of a tool with a linear element, such as for example a flat head screwdriver. A cam follower 52 is mounted on post 51, such that cam follower 52 resides within cam opening 46 on the engagement arm 41 when the post member 51 is properly disposed in the second clamp member body 21.

The main body 11 of the first clamp member 10 is provided with an extended ratchet bar member 13 having a row of engagement teeth 14, which comprise another component of the engagement means 40. The clamp engagement teeth 14 are configured so as to interact or mate with the engagement teeth 42 of the engagement arm 41. Both the clamp engagement teeth 14 and the arm engagement teeth 42 each have an inclined side 61 and a generally more perpendicular, i.e., less angled, abutment side 62, with the inclined sides 61a of the engagement arm 41 facing the inclined sides 61b of the ratchet bar 13, and the abutment sides 62a of the engagement arm 41 facing the abutment sides 62b of the ratchet bar 13. The inclined sides 61 are disposed such that they come into direct contact with each other, yet may pass slidingly over each other when the sternal clamp 100 is set in the closing status and contraction or shortening of the sternal clamp 100 is attempted. The abutment sides 62 are disposed such that they contact each other and prevent lengthening of the sternal clamp 100 when in the locked status or closing status. In the open status, neither the inclined surfaces 61 nor the abutment sides 62 contact each other when the clamp members 10 and 20 are compressed or lengthened.

The status control means 50 is rotatable over approximately 180 degrees such that the cam follower 52 likewise rotates approximately 180 degrees within the cam opening 46. In a first position, designated as the open status and shown in FIG. 2 and at position "O" of FIG. 5, the cam follower 52 abuts the cam opening 46 such that the engagement arm 41 is pivoted toward the spring body 44 and maintained in a position separated from the ratchet bar 13 of the first clamp member 10, such that the arm engagement teeth 42 and the clamp engagement teeth 14 are not in contact and the clamp members 10 and 20 can be freely moved in either direction.

Figure 1:
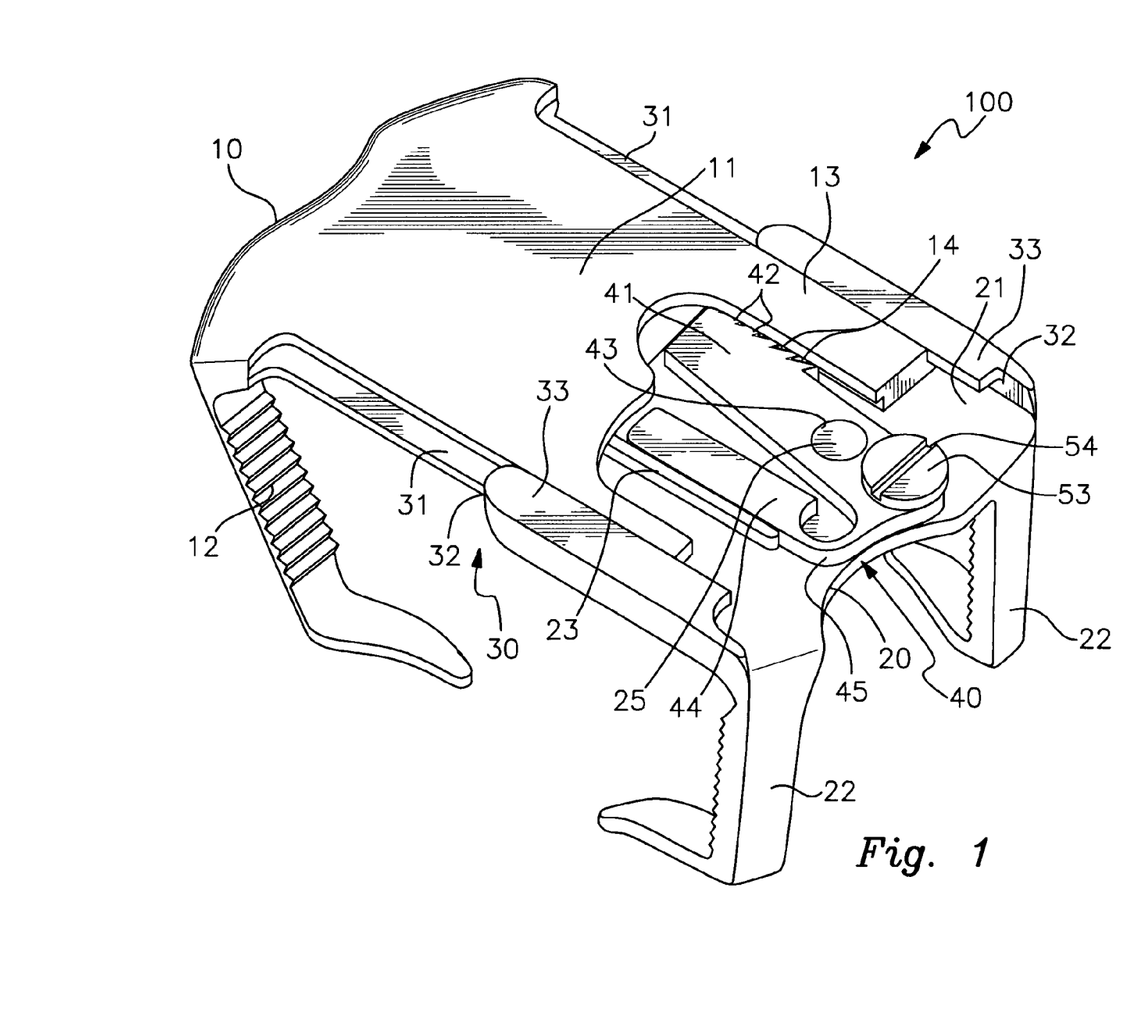
FIG. 1 is a perspective view of the invention shown in the locked status.
Figure 2:
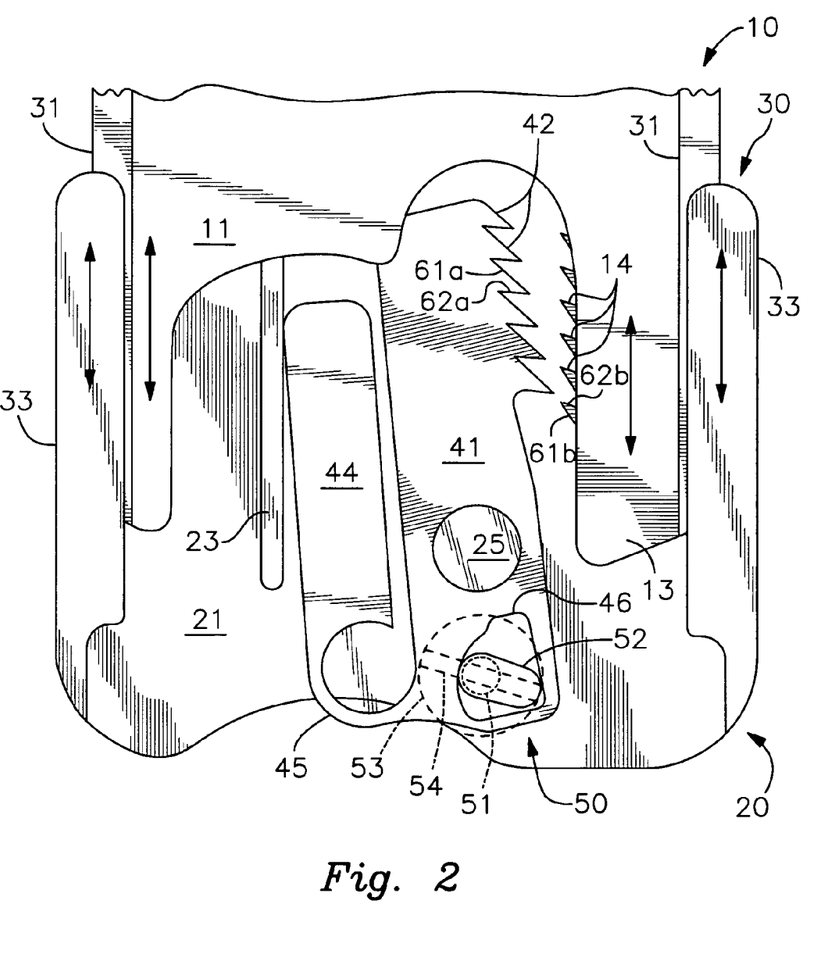
FIG. 2 is a partial front view of the invention shown in the open status, where the head of the status control means is shown in outline to expose the cam opening and the cam follower.
Figure 3:
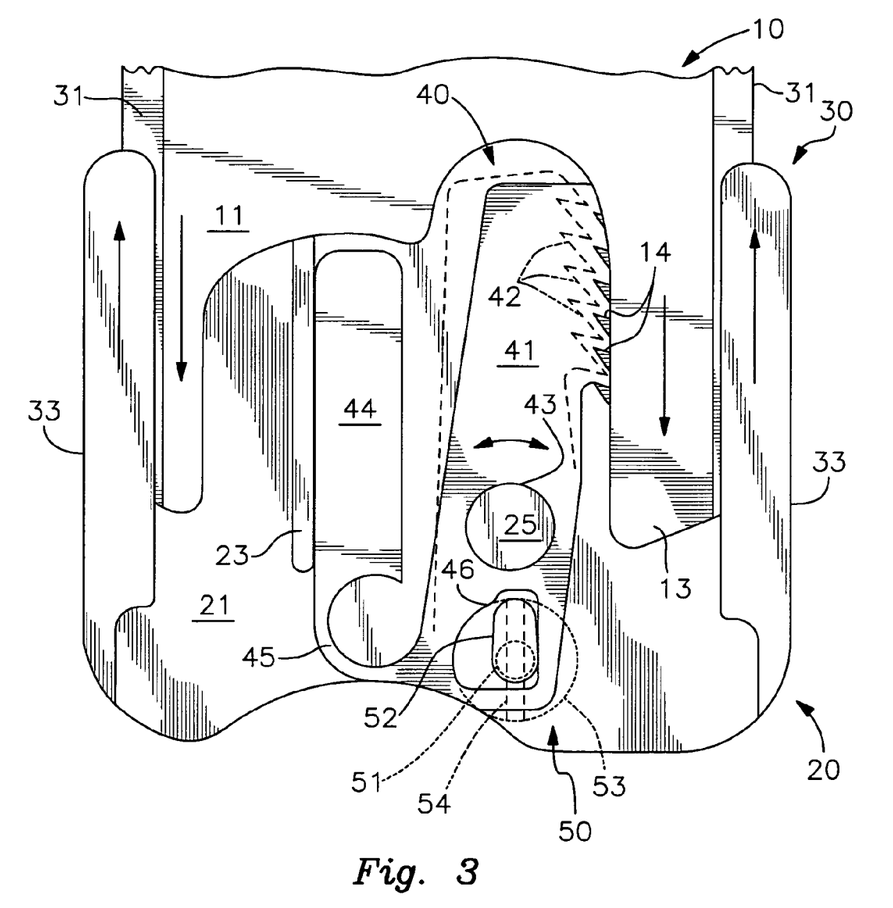
FIG. 3 is a view of the invention similar to FIG. 2, where the invention is shown in the closing status.
Figure 5:
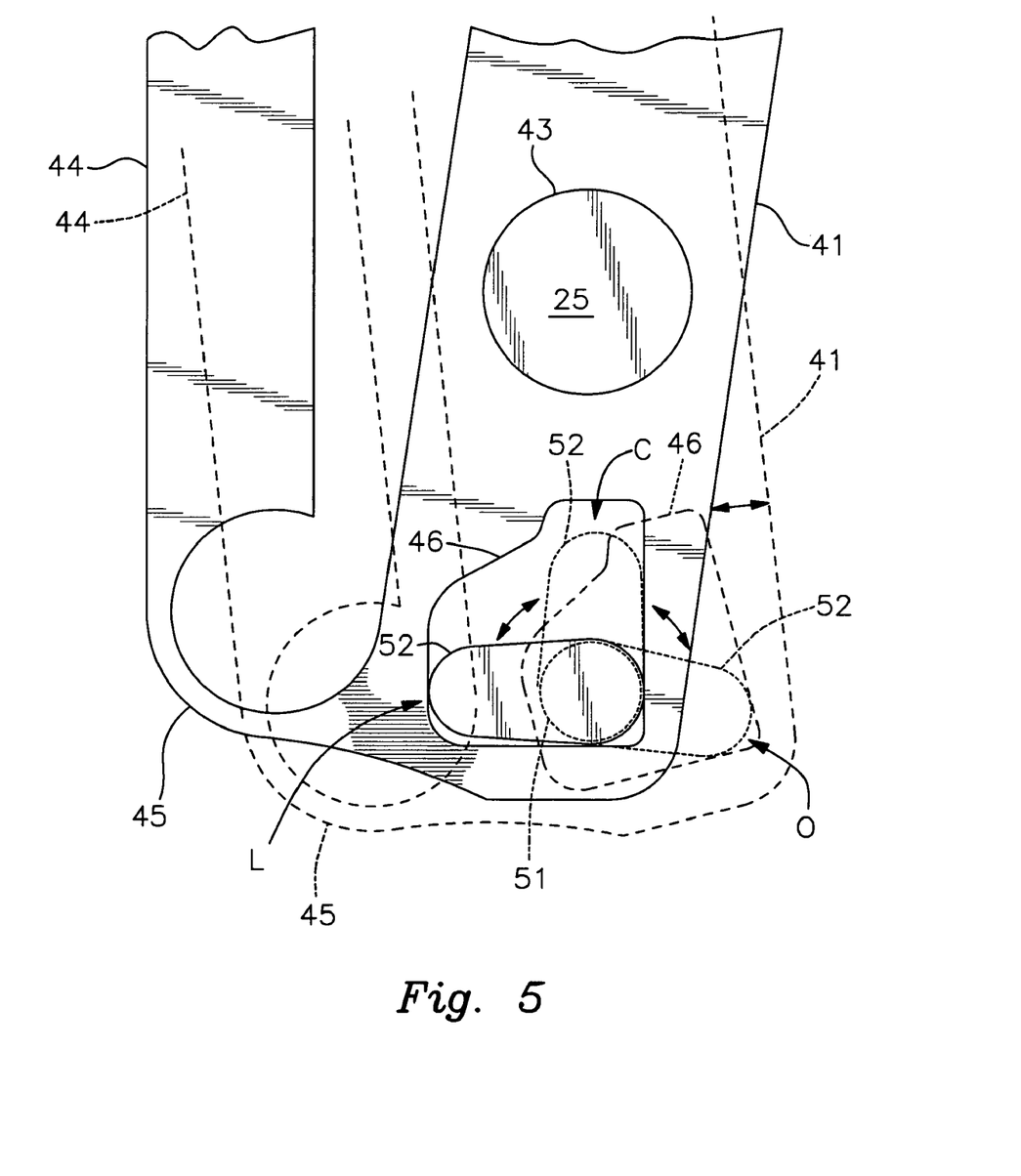
FIG. 5 is a view of certain elements of the engagement means and the status control means, illustrating the relative positions of the engagement arm and spring body for the open, closing and locked positions of the cam follower, designated as O, C and L.
Figure 6:
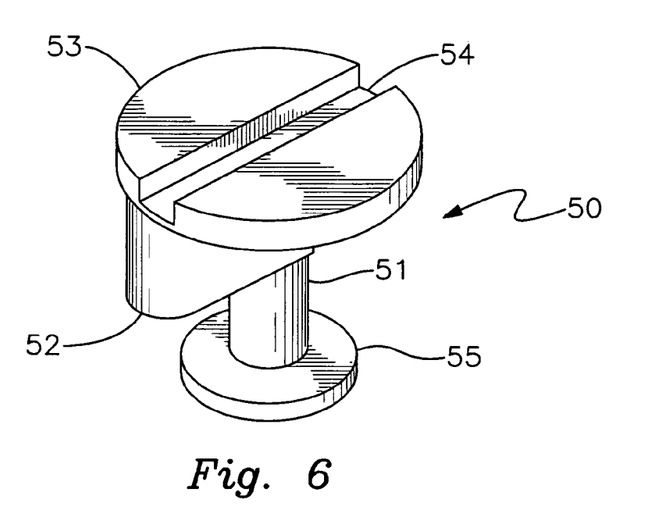
FIG. 6 is a perspective view of the status control means.
Figure 7:
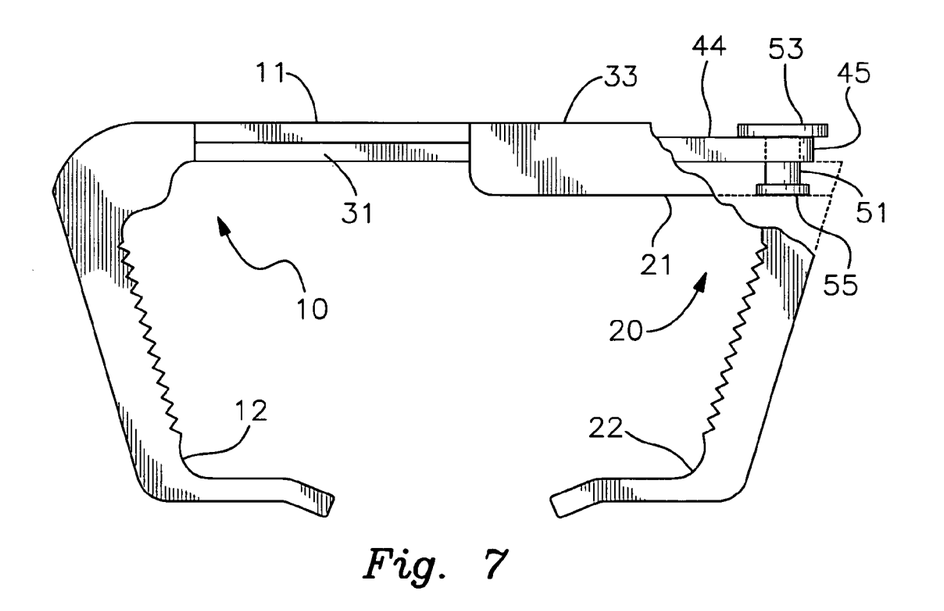
FIG. 7 is a side view of the invention with a portion of the second clamp members removed to expose the status control means.

In a second position, designated as the closing status and shown in FIG. 3 and at position "C" of FIG. 5, the cam follower 52 is positioned within the cam opening 46 such that a small amount of pivoting movement of the engagement arm 41 is permitted away from the ratchet bar member 13 of the first clamp member 10, as illustrated by the dashed lines of FIG. 2. In this status, the clamp members 10 and 20 can be moved so as to shorten the sternal clamp, the sliding contact of the inclined sides 61 of the engagement teeth 42 and 14 causing the engagement arm 41 to be forced a small distance backward against the biasing force of the spring 45 as the clamp members 10 and 20 are contracted, the inclined sides 61 allowing the teeth 14 and 42 to fully slide over each other. Movement of the clamp members 10 and 20 in an attempt to lengthen the sternal clamp 100, however, is precluded by contact between the more perpendicular abutment sides 62 of engagement teeth 42 and 14, since these sides are negatively inclined and no ramping effect is created to slide across each other.

Figure 4:
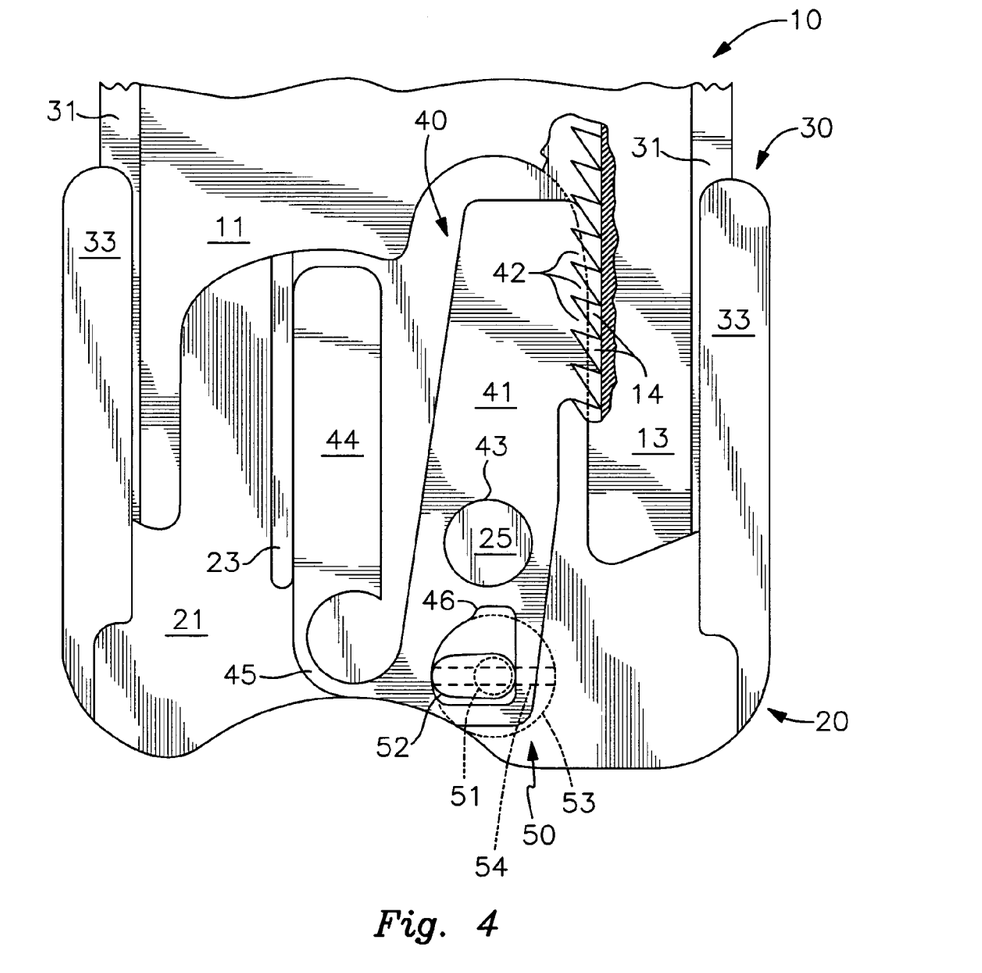
FIG. 4 is a view of the invention similar to FIG. 2 or 3, where the invention is shown in the locked status and a portion of the ratchet bar has been removed to expose the ratchet bar teeth.

In the third position, designated as the locked status and shown in FIG. 4 and as position "L" in FIG. 5, the cam follower 52 is positioned across the cam opening 46 such that the engagement arm 41 is maintained in a fixed position and prevented from pivoting in either direction. In this status, the sternal clamp 100 can be neither lengthened nor shortened, as the engagement teeth 42 and 14 cannot be separated sufficient distance to allow relative movement of the clamp members 10 and 20, even in the direction of the inclined sides 61. The sternal clamp 100 may be disposed in the locked status over a plurality of differing overall lengths.

In this manner, the lock and release mechanism provides for a sternal clamp 100 that can be easily assembled, positioned across the gapped sternum, contracted to secure the separated sternal halves, and locked in the compressed or shortened configuration to maintain the sternal halves in an abutting relation. In the event that the sternal clamp 100 must be rapidly removed, the status control means 50 is easily rotated to the open status position, thereby retracting the engagement arm 41 from contact with the ratchet bar 13 and allowing the two clamp members 10 and 20 to elongated and completely separated for removal.

It is understood and contemplated that equivalents or substitutions for descriptive elements set forth above may be obvious to those skilled in the art, and therefore the true scope and definition of the invention is to be as set forth in the following claims.

I claim:

1. A sternal clamp device comprising:
a first clamp member and a second clamp member slidingly engaged such that the overall length of said sternal clamp device may be shortened or lengthened by relative movement of said first and second clamp members, each said clamp member comprising at least one leg member to abut the sides of a sternum;
engagement means controlling relative movement of said first and second clamp members, wherein said engagement means comprises a biased engagement arm having a plurality of teeth, said engagement arm disposed on said second clamp member, and a ratchet bar having a plurality of teeth, said ratchet bar disposed on said first clamp member, whereby said engagement arm teeth and said ratchet bar teeth are able to engage with each other; and
status control means to select one of three operating statuses for said sternal clamp device, said operating statuses consisting of an open status, a closing status and a locked status, wherein said status control means comprises a cam opening disposed in said engagement arm and a rotatable cam follower positioned within said cam opening, whereby selection of said operating status and biasing of said engagement arm is determined by the position of said cam follower;
whereby in said open status said sternal clamp device may be lengthened or shortened, in said closing status said sternal clamp device may be shortened but not lengthened, and in said locked status said sternal clamp may be neither lengthened nor shortened;
and further whereby said sternal clamp device may be disposed in said locked status in differing overall lengths.

2. The device of claim 1, wherein said engagement arm is pivotally mounted, such that in said locked status said engagement arm is precluded from pivoting away from said ratchet bar, in said closing status said engagement arm can pivot sufficient distance from said ratchet bar to allow said engagement arm teeth and said ratchet bar teeth to slide over each other, and in said open status said engagement arm is held in a fixed position away from said ratchet bar such that said engagement arm teeth and said ratchet bar teeth are not in contact.

3. The device of claim 1, wherein said status control means further comprises a post member retaining said cam follower, a head member disposed on said post member and a slot disposed in said head member, said post member being rotatably mounted in said second clamp member.

4. The device of claim 1, wherein said engagement arm teeth each have an inclined side and an abutment side, said abutment sides being more perpendicularly oriented than said inclined sides, and wherein said ratchet bar teeth each have an inclined side and an abutment side, said abutment sides being more perpendicularly oriented than said inclined sides, whereby the inclined sides of said engagement arm teeth and said ratchet bar teeth face each other and the abutment sides of said engagement arm teeth and said ratchet bar teeth face each other.

5. A sternal clamp device comprising:
a first clamp member and a second clamp member to engage the sides of a sternum;
sliding means joining said first and second clamp members together whereby said sternal clamp can be lengthened or shortened;
engagement means to restrict relative motion of said first and second clamp members, wherein said engagement means comprises a biased engagement arm having a plurality of teeth, said engagement arm disposed on said second clamp member, and a ratchet bar having a plurality of teeth, said ratchet bar disposed on said first clamp member, whereby said engagement arm teeth and said ratchet bar teeth are able to engage with each other;
status control means to control said engagement means, said status control means being operable in a locked status, a closing status and an open status, wherein said status control means comprises a cam opening disposed in said engagement arm and a rotatable cam follower positioned within said cam opening, whereby selection of said operating status and biasing of said engagement arm is determined by the position of said cam follower;

whereby said status control means disposed in said locked status precludes relative movement of said first and said second clamp members, disposed in said closing status allows relative movement of said first and said second clamp members together so as to shorten said sternal clamp but precludes relative movement of said first and second clamp members apart so as to lengthen said sternal clamp, and disposed in said open status allows relative movement of said first and said second clamp members both together and apart;

and further wherein said sternal clamp device may be disposed in said locked status in differing overall lengths.

6. The device of claim 5, wherein said engagement arm is pivotally mounted, such that in said locked status said engagement arm is precluded from pivoting away from said ratchet bar, in said closing status said engagement arm can pivot sufficient distance from said ratchet bar to allow said engagement arm teeth and said ratchet bar teeth to slide over each other, and in said open status said engagement arm is held in a fixed position away from said ratchet bar such that said engagement arm teeth and said ratchet bar teeth are not in contact.

7. The device of claim 5, wherein said status control means further comprises a post member retaining said cam follower, a head member disposed on said post member and a slot disposed in said head member, said post member being rotatably mounted in said second clamp member.

8. The device of claim 5, wherein said engagement arm teeth each have an inclined side and an abutment side, said abutment sides being more perpendicularly oriented than said inclined sides, and wherein said ratchet bar teeth each have an inclined side and an abutment side, said abutment sides being more perpendicularly oriented than said inclined sides, whereby the inclined sides of said engagement arm teeth and said ratchet bar teeth face each other and the abutment sides of said engagement atm teeth and said ratchet bar teeth face each other.

9. A sternal clamp device configured for securing two severed halves of a sternum in abutting relation, said device comprising:

a first clamp member comprising a main body and at least one leg member;

a second clamp member comprising a main body and at least one leg member, said second clamp member joined to said first clamp member in a sliding manner whereby said sternal clamp device may be lengthened by relative movement of said first and second clamp members away from each other and whereby said sternal clamp device may be shortened by relative movement of said first and second clamp members toward each other;

such that said sternal clamp device is configured to be lengthened and positioned on sternal halves with said leg members of said first and second clamp members to either side of the sternal halves, and such that said sternal clamp device is configured to be shortened in order to force the sternal halves together;

engagement means to control relative movement of said first and said second clamp members, wherein said engagement means comprises a biased engagement arm having a plurality of teeth, said engagement arm disposed on said second clamp member, and a ratchet bar having a plurality of teeth, said ratchet bar disposed on said first clamp member, whereby said engagement arm teeth and said ratchet bar teeth are able to engage with each other;

status control means to control said engagement means, whereby said engagement means is set in one of three operating statuses, a locked status wherein relative movement of said first and said second clamp members is precluded and wherein said sternal clamp device may be disposed in said locked status in differing overall lengths, a closing status wherein relative movement of said first and said second clamp members toward each other is allowed but relative movement away from each other is precluded, and an open status wherein relative movement of said first and said second clamp members in either direction is allowed, wherein said status control means comprises a cam opening disposed in said engagement arm and a rotatable cam follower positioned within said cam opening, whereby selection of said operating status and biasing of said engagement arm is determined by the position of said cam follower.

10. The device of claim 9, wherein said engagement arm is pivotally mounted, such that in said locked status said engagement arm is precluded from pivoting away from said ratchet bar, in said closing status said engagement arm can pivot sufficient distance from said ratchet bar to allow said engagement arm teeth and said ratchet bar teeth to slide over each other, and in said open status said engagement arm is held in a fixed position away from said ratchet bar such that said engagement arm teeth and said ratchet bar teeth are not in contact.

11. The device of claim 9 wherein said status control means further comprises a post member retaining said cam follower, a head member disposed on said post member and a slot disposed in said head member, said post member being rotatably mounted in said second clamp member.

12. The device of claim 9, wherein said engagement arm teeth each have an inclined side and an abutment side, said abutment sides being more perpendicularly oriented than said inclined sides, and wherein said ratchet bar teeth each have an inclined side and an abutment side, said abutment sides being more perpendicularly oriented than said inclined sides, whereby the inclined sides of said engagement arm teeth and said ratchet bar teeth face each other and the abutment sides of said engagement arm teeth and said ratchet bar teeth face each other.

* * * * *